United States Patent [19]

Legrow

[11] Patent Number: 5,232,693
[45] Date of Patent: Aug. 3, 1993

[54] METHOD OF TREATING DRY SKIN

[75] Inventor: Gary E. Legrow, Midland, Mich.

[73] Assignee: Dow Corning Corporation, Midland, Mich.

[21] Appl. No.: 848,605

[22] Filed: Mar. 9, 1992

[51] Int. Cl.$^5$ .......................................... A61K 31/765
[52] U.S. Cl. .................................. 424/78.37; 424/401; 514/887
[58] Field of Search ............... 424/401, 47, 78.37; 514/847, 873, 844, 947; 556/453; 106/287.14, 287.15, 286.16; 252/173

[56] References Cited

U.S. PATENT DOCUMENTS

| | | | |
|---|---|---|---|
| 3,392,040 | 7/1968 | Kass | 106/287.15 |
| 3,632,619 | 1/1972 | Groenhof | 260/448.2 |
| 3,756,052 | 9/1973 | Quaal et al. | 72/42 |
| 3,885,984 | 5/1975 | Wright | 106/287.14 |
| 4,054,670 | 10/1977 | Buhler | 514/873 |
| 4,230,632 | 10/1980 | Chapman | 556/453 |
| 4,364,837 | 12/1982 | Pader | 252/173 |
| 4,421,769 | 12/1983 | Dixon et al. | 514/847 |
| 4,906,458 | 3/1990 | Shigeta et al. | 424/63 |
| 4,973,476 | 11/1990 | Krzysik | 424/71 |
| 4,980,167 | 12/1990 | Harashima et al. | 424/401 |
| 5,017,221 | 5/1991 | Legrow et al. | 106/287:15 |
| 5,035,890 | 7/1991 | Braun | 424/401 |
| 5,068,277 | 11/1991 | Vukov et al. | 106/287.14 |

Primary Examiner—Thurman K. Page
Attorney, Agent, or Firm—James L. Decesare

[57] ABSTRACT

A method of treating human skin by topically administering an alkylmethylpolysiloxane having the formula

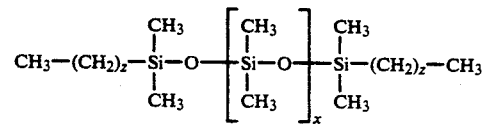

in which x has a value of 1–300 and z has a value of 5–50.

3 Claims, No Drawings

METHOD OF TREATING DRY SKIN

BACKGROUND OF THE INVENTION

This invention relates to a method of treating dry human skin by the topical administration of certain alkylmethylpolysiloxanes.

The water content of the outer layers of the stratum corneum of human skin is a controlling factor in the appearance of dry skin symptoms. When the stratum corneum contains an adequate amount of water within the range of ten to twenty percent the skin remains flexible. However when the water content falls below ten percent the stratum corneum often becomes brittle and rough and can exhibit scaling and cracking.

The stratum corneum receives its water from the deep layers of the epidermis by diffusion or when it is brought into direct contact with water. The diffusion process is controlled by the water content of the skin as well as the concentration gradient. In a very dry environment the water loss from the external skin layers can be significant and often exceeds the rate of replacement by diffusion. An occlusive barrier placed onto the surface of the skin acts to retard the water loss to the environment and allows the skin to rehydrate by the diffusion process.

The convenient availability and low cost of nonprescription drugs and over-the-counter medicines has spawned an increase in responsible consumer self-medication in the field of dry skin treatment. Numerous dry skin preparations are available. Typical dermatological moisturizers containing one or more emollients can be found marketed under trademarks such as EUCERIN® and NIVEA® by Beiersdorff Incorporated, Norwalk, Conn.; KERI® by Westwood Pharmaceuticals Incorporated, Buffalo, N.Y.; LUBRIDERM® by Warner-Lambert Company; and NEUTROGENA® by Neutrogena Corporation, Los Angeles, Calif.

The present invention provides a dry skin preparation containing certain alkylmethylendblocked polysiloxanes which has been found to alleviate the symptoms of dry skin more effectively than some of the currently available over-the-counter dermatological formulations. While alkylmethylendblocked siloxanes are known in the prior art as evidenced by U.S. Pat. Nos. 3,632,619 issued Jan. 4, 1972; 3,756,052 issued Sep. 4, 1973; and 4,973,476 issued Nov. 27, 1990; their use in the treatment of dry skin in the fashion contemplated by the present invention is not disclosed.

SUMMARY OF THE INVENTION

The invention is directed to a skin treatment method in which the symptoms of dry skin are alleviated by the topical application to the skin of a dermatological formulation which consists of only an alkylmethylendblocked polysiloxane.

It is an object of the present invention to provide a skin care composition which will effectively protect all skin types from dryness.

It is a further object of the present invention to provide a skin treatment which is long-lasting, safe, and which will soften and moisturize the skin leaving it supple.

It is an additional object of the present invention to provide an effective skin protectant which is nonirritating and nonsensitizing.

These and other features, object and advantages of the herein described present invention will become more apparent from a consideration of the following detailed description thereof.

DETAILED DESCRIPTION OF THE INVENTION

There are two types of dry skin. The first is caused by prolonged exposure to low humidity and low temperature with the result that the drying stress increases to such an extent that the normal hydration gradient of the stratum corneum is modified. The second type of dry skin is caused by the modification of the normal hydration gradient as a result of physical or chemical changes of the skin such as aging and in cases of pathological skin dryness.

Materials, preparations and formulations which seek to correct the condition of loss of skin flexibility due to dryness are termed emollients. Emollient formulations are available in a wide variety of delivery forms such as emulsions, microemulsions, dispersions, gels, aerosols, stick products, ointments, lotions, creams, solutions, sprays, and oils. Since water is an essential emollient, many of these products function by either facilitating the process of rehydration or by the prevention of subsequent dehydration. Typically, such products function by a purely physical mechanism although in some cases the mechanism may be physiological.

In accordance with the present invention, dry skin is treated by rubbing onto the affected area an alkylmethylpolysiloxane having the formula

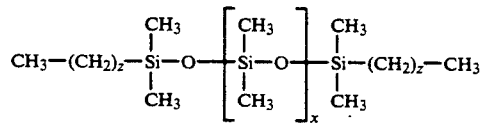

in which x has a value of 1–300 and z has a value of 5–50. Preferably, x has a value of 6–24 and z has a value of 22–28. Most preferably, x has an average value of 12 and z has an average value of 26.

The method in accordance with the present invention consists of administering the alkylmethylpolysiloxane "neat" to the affected skin. By "neat" is meant that ingredients normally present in skin conditioning formulations are not compatible with the method of the present invention. Thus, other than normal impurities present in the alkylmethylpolysiloxanes, the skin treatment formulation of the present invention is free of solvents, emulsifiers, emollients, antioxidants, thickeners, neutralizers, moisturizers, humectants, and buffers for example. The skin treatment formulation may however tolerate minor amounts of ingredients required to market a product which is aesthetically pleasant to the consumer such as a fragrance or colorant.

Alkylmethylpolysiloxanes are commercially available materials and can be produced by methods known in the prior art. Cyclic alkylmethylpolysiloxanes are produced by the reaction of a cyclic siloxane possessing Si-H functional units such as $(MeHSiO)_x$ with a slight stoichiometric excess of an alkene in the presence of a platinum on carbon catalyst. Linear and cyclic alkylmethylpolysiloxanes are produced by the reaction of a linear siloxane possessing SiH functionality in the chain such as $(Me_3SiO_{0.5})_2(MeHSiO)_x$ and a cyclic siloxane having $(Me_2SiO)_x$ units. The reaction product typically includes about ten percent of cyclic siloxane and about ninety percent of linear siloxane and is contacted with a slight excess of an alkene in the presence of a platinum on carbon catalyst.

Batch production of the alkylmethylpolysiloxanes can be conducted by the addition of the reaction product to a nonagitated suspension of the catalyst in the alkene at a temperature of about sixty degrees Centigrade. Continuous production can be conducted by pumping a preheated solution of a stoichiometric excess of the alkene $CH_2=CHR$ and the reaction product through a packed column containing platinum on carbon catalyst in the form of chips. Because of the exothermic nature of the reaction, the column requires some provision for the removal of heat. Alkylmethylpolysiloxanes according to the present invention must be further processed in order to provide a cosmetically acceptable product by the removal of any residual cyclic siloxane or any residual methylhydrogendimethylsiloxane cocyclics which may be present as $(MeHSiO)(Me_2SiO)_3$. For the purposes of the present invention, the alkylmethylpolysiloxanes should contain no measurable residual amount of platinum, and at most about 0.5 percent residual alkene resulting in a product which is about 99.5 percent alkylmethylpolysiloxane.

When applied in accordance with the present invention, the alkylmethylendblocked polysiloxane alleviates severely dry skin and restores it to near normal condition within a few days when administered "neat" to the affected skin area of the body. The alkylmethylsilicone material of preference is a wax having a softening point between room temperature of about twenty degrees Centigrade and normal skin temperature of about thirty-three degrees Centigrade. The average composition of the preferred material is $C_{26}H_{53}Me_2SiO(Me_2SiO)_{12}SiMe_2C_{26}H_{53}$. As noted previously, the number of $(Me_2SiO)$ units may range from 1-300 but preferably have a value within the range of about 6-24. The endblocking units include an alkyl group which may have from 22-28 carbon atoms as indicated above. An increase in the number of carbon atoms beyond twenty-six is generally not suitable in accordance with the present invention. Thus, an increase to $C_{30}$ for example increases the softening point of the wax material to an excess of fifty degrees Centigrade rendering its spreadability on the skin surface more difficult.

The concept of the present invention was demonstrated by in vivo testing of the silicone materials. The subjects tested had a history of severe dry skin problems for more than seven years. Their history indicated that skin dryness was less during humid summer months than during dry winter months. In the winter, the test subjects indicated that skin dryness at its worst was manifested by cracks in the stratum corneum accompanied by frequent bleeding particularly when there had been exposure to water and detergents or when the skin was dry and physically abraded.

In vivo testing consisted of applying "neat" to the affected skin areas of the test subjects the compound $C_{26}H_{53}Me_2SiO(Me_2SiO)_{12}SiMe_2C_{26}H_{53}$. A light application of the compound was administered to the skin daily for a period of one week. Within a few days the test subjects reported that the affected skin areas exhibited signs of crack recession and that by the end of the week, cracks had disappeared and that the normal dry appearance of the skin had virtually disappeared.

The test subjects reported that commercially available over-the-counter products as well as prescription preparations intended to alleviate dry skin had been used by the test subjects at various times over the previous five years, but that regular daily application of these materials had not provided any relief. The test subjects reported that the commercially available over-the-counter products included (i) a water in oil emulsion containing water, petrolatum, and mineral oil marketed by Beiersdorf Incorporated, Norwalk, Conn. under the trademark EUCERIN ®; (ii) an emulsion containing water, glycerin, aloe vera gel and mineral oil marketed by Chesebrough-Ponds Incorporated, Greenwich, Conn. under the trademarks VASELINE ® INTENSIVE CARE ® LOTION; and prescription preparations (iii) 0.1% Halog containing halcinonide which is an adrenocorticoid for topical application; (iv) 0.05% Psorcon Ointment containing diflorasone diacetate; and (v) 2.5% Hydrocortisone Cream.

The following examples are set forth for the purpose of illustrating a method of preparing alkylmethylpolysiloxane materials suitable for use in accordance with the present invention.

EXAMPLE I

Into a container there was added ten grams of a platinum on carbon catalyst and 430 grams of a ninety-five percent pure C24 to C28 alpha olefin fraction. The alpha olefin fraction was a blend of alpha olefins containing a weight distribution of mixed C22 to C30 alpha olefins with (i) one percent being C22; (ii) thirty percent being C24; (iii) thirty-nine percent being C26; (iv) twenty percent being C28; and (v) ten percent being C30+. The C24 to C28 alpha olefin fraction is a product of the Chevron Chemical Company, Houston, Tex., and is sold under the trademark GULFTENE ® 24–28. The container contents were heated to one hundred degrees Centigrade accompanied by slow stirring and there was added 55 grams of mixed cyclic siloxanes of the formula $(Me_2SiO)_x$ in which x was four to six, and 570 grams of the methylhydrogensiloxane $HMe_2SiO(Me_2SiO)_{12}SiMe_2H$. The slurry was stirred for one hour at one hundred degrees Centigrade and cooled to fifty degrees Centigrade. While at fifty degrees Centigrade the slurry was filtered to remove the catalyst. The container was heated to 150 degrees Centigrade at one millimeter to remove the cyclic siloxane mixture. The recovered alkylmethylpolysiloxane product was a soft wax.

EXAMPLE II

Example I was repeated except that 1-octadecene was employed in place of the C24 to C28 alpha olefin fraction GULFTENE ® 24–28. The product recovered was a liquid alkylmethylpolysiloxane $C_{18}H_{37}Me_2SiO(Me_2SiO)_{12}SiMe_2C_{18}H_{37}$.

EXAMPLE III

Example I was repeated except that in place of the C24 to C28 alpha olefin fraction GULFTENE ® 24–28, there was employed a C28 to C30 alpha olefin fraction. The alpha olefin fraction was a blend of alpha olefins containing a weight distribution of mixed C28 to C30+ alpha olefins with 28 percent being C28 and 78 percent being C30+. The C28 to C30+ alpha olefin fraction is a product of the Chevron Chemical Company, Houston, Tex., and is sold under the trademark GULFTENE ® 30+. The product recovered was an alkylmethylpolysiloxane which was a high melting point wax.

EXAMPLE IV

A 1:1 molar blend of the products of Examples II and III was produced by heating 55 grams of the high melting point was product of Example III to a liquid state and adding 45 grams of the liquid product of Example II. Upon cooling, the product blend provided a soft wax alkylmethylpolysiloxane which exhibited the same consistency as the soft wax of Example I.

It will be apparent from the foregoing that many other variations and modifications may be made in the compounds, compositions and methods described herein without departing substantially from the essential features and concepts of the present invention. Accordingly, it should be clearly understood that the forms of the invention described herein are exemplary only and are not intended as limitations on the scope of the present invention as defined in the appended claims.

That which is claimed is:

1. A method comprising rubbing onto dry human skin a composition consisting of an alkylmethylpolysiloxane having the formula

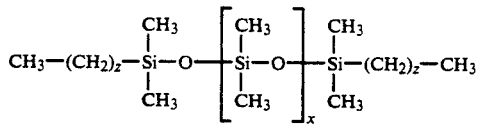

in which x has a value of 1–300 and z has a value of 22 to 28.

2. A method according to claim 1 in which x has a value of 6–24 and.

3. A method according to claim 2 in which x has a value of 12 and z has a value of 26.